(12) United States Patent
Dalton

(10) Patent No.: US 6,884,224 B2
(45) Date of Patent: Apr. 26, 2005

(54) NEEDLE PROTECTION DEVICE

(75) Inventor: Michael J. Dalton, Evanston, IL (US)

(73) Assignee: Norfolk Medical, Skokie, IL (US)

( * ) Notice: Subject to any disclaimer, the term of this patent is extended or adjusted under 35 U.S.C. 154(b) by 12 days.

(21) Appl. No.: 10/407,486

(22) Filed: Apr. 4, 2003

(65) Prior Publication Data

US 2004/0199112 A1 Oct. 7, 2004

(51) Int. Cl.$^7$ ................................................. A61B 5/00
(52) U.S. Cl. ........................ 600/573; 604/192; 604/110; 604/263
(58) Field of Search .................. 600/573, 575–579, 600/581; 604/110, 115, 117, 162, 164.08, 263, 192–199; 606/181–183

(56) References Cited

U.S. PATENT DOCUMENTS

| | | | | |
|---|---|---|---|---|
| 4,725,267 A | * | 2/1988 | Vaillancourt | 604/192 |
| 4,850,961 A | * | 7/1989 | Wanderer et al. | 604/508 |
| 4,911,706 A | | 3/1990 | Levitt | 604/198 |
| 5,092,851 A | | 3/1992 | Ragner | 604/192 |
| 5,120,321 A | * | 6/1992 | Oksman et al. | 604/198 |
| 5,147,327 A | | 9/1992 | Johnson | 604/198 |
| 5,295,963 A | * | 3/1994 | Deeks | 604/110 |
| 5,364,370 A | * | 11/1994 | Szerlip et al. | 604/192 |
| 5,554,131 A | | 9/1996 | Lacivita | 604/198 |
| 5,688,241 A | * | 11/1997 | Asbaghi | 604/110 |
| 5,700,249 A | | 12/1997 | Jenkins | 604/263 |
| 5,713,872 A | | 2/1998 | Feuerborn | 604/192 |
| 5,817,070 A | | 10/1998 | Tamaro | 604/263 |
| 5,885,255 A | | 3/1999 | Jaeger, Jr. | 604/192 |
| 5,984,899 A | | 11/1999 | D'Alessio | 604/198 |
| 6,210,373 B1 | | 4/2001 | Allmon | 604/192 |
| 6,254,577 B1 | | 7/2001 | Huet | 604/192 |
| 6,613,015 B1 | * | 9/2003 | Sandstrom et al. | 604/110 |
| 2002/0055711 A1 | * | 5/2002 | Lavi et al. | 604/110 |

OTHER PUBLICATIONS

Clear–View "Sub–Q" Promotional Document, Norfolk Medical, Sep. 10, 2001, 2 pages.

* cited by examiner

*Primary Examiner*—Charles Marmor
(74) *Attorney, Agent, or Firm*—Cardinal Law Group

(57) ABSTRACT

A needle safety and protection device that automatically caps the used tip of a needle the instant the needle is withdrawn from the patient to protect the user against infection risks. A spiral type cut safety shield remains relaxed until the device comes in contact with the patient's skin. The safety shield attaches to the patent's skin through an adhesive component creating a tensile force once the needle is withdrawn, extending the safety disk out of its relaxed position. Under tension, the safety disk creates a cone around the needle, forming a protective shield for the needle, without any assistance by the user. The tip of the needle then engages a portion of the shield, which prevents the tip from being re-inserted into the skin of the patient or the user of the needle.

14 Claims, 5 Drawing Sheets

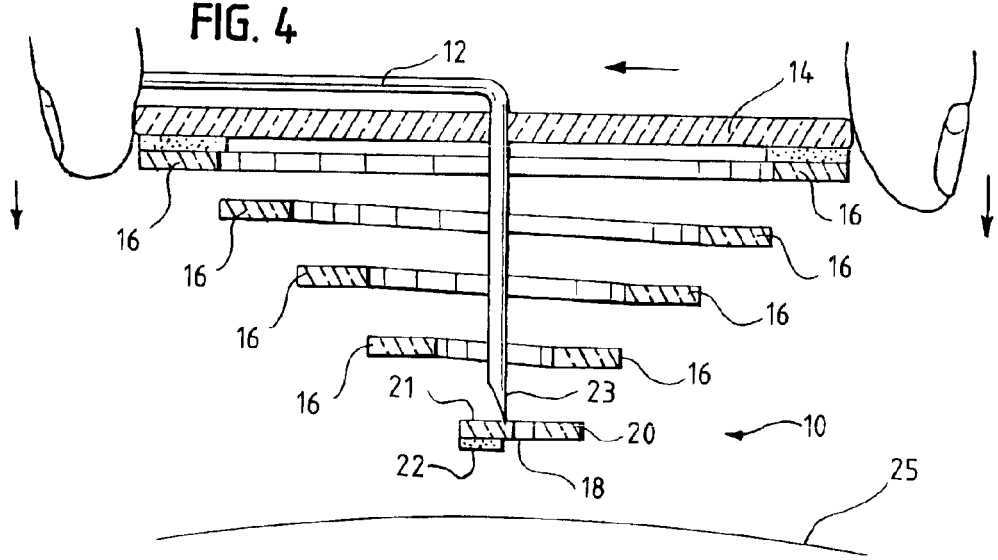
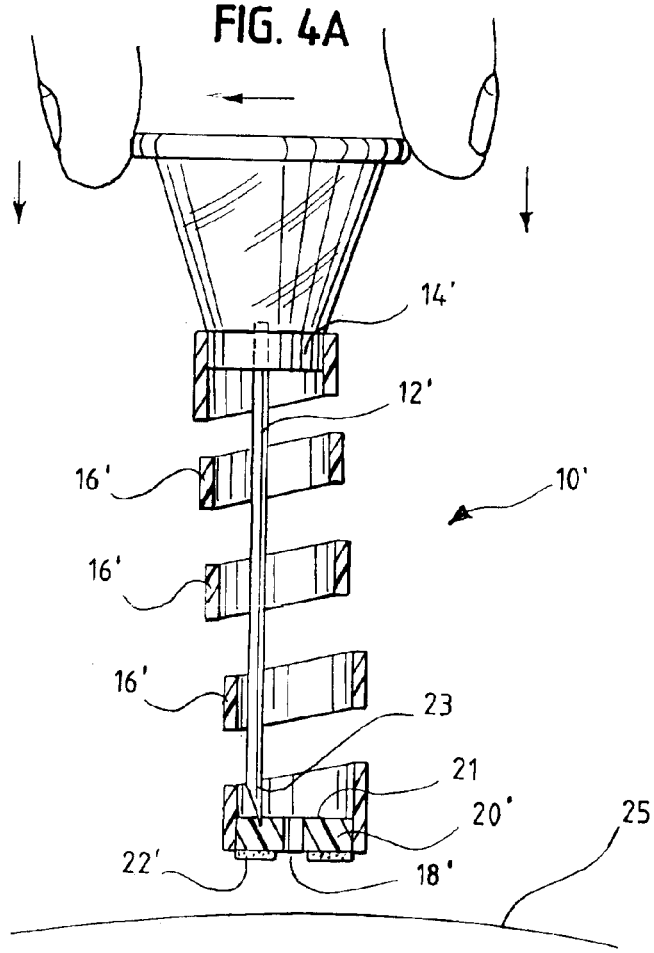

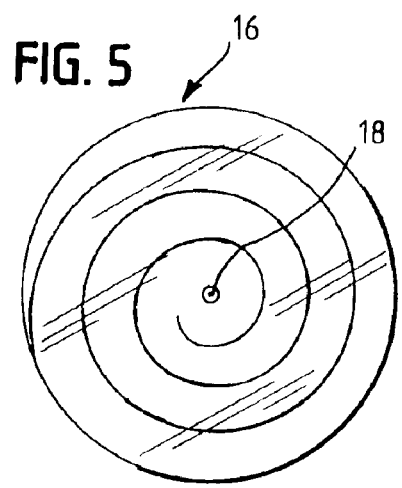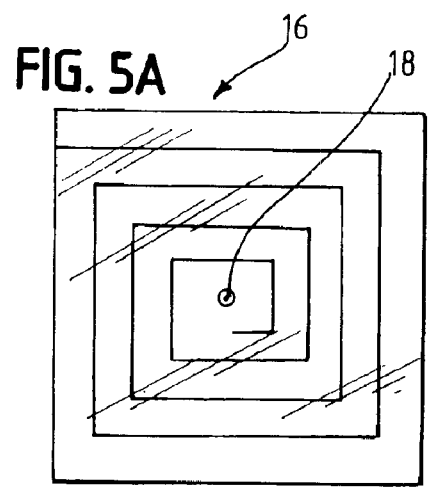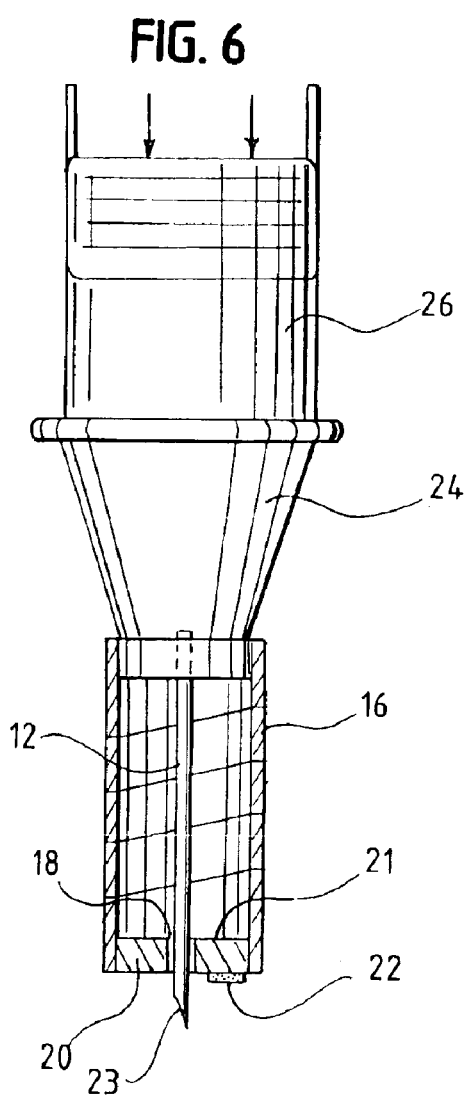

NEEDLE PROTECTION DEVICE

BACKGROUND OF THE INVENTION

The present invention is an improved device for protecting users from needle sticks by automatically capping the used needle the instant the needle is withdrawn from the patient to protect the user against infection risks.

DESCRIPTION OF RELATED ART

Needles are used in the medical industry to deliver medications or to draw blood for diagnosis. United States health authorities estimate that some 600,000 to 800,000 accidental needle stick injuries occur every year. There are roughly 8,000,000 healthcare workers in the United States who are at risk of being stuck with a needle that is contaminated with AIDS, Hepatitis, Herpes, Tuberculosis, Fungi and a full range of infectious microorganisms.

The purpose of this invention is to address the problem of transmission of diseases as a result of user contact with used needles. Although currently there exist various needle protection devices, most require the user to take an affirmative step thereby causing potential risk of contact with the needle. This invention, however, automatically shields the needle tip the moment the needle is withdrawn from the patient without any affirmative step required on the part of the user.

Currently, there are not any needle protection devices that address the issues faced by subcutaneous needles. This needle protection device allows for the automatic recapping of subcutaneous needles as well as needles of nearly every length and gauge. An additional purpose of this invention is to provide the user protection for used subcutaneous needles.

SUMMARY OF THE INVENTION

This invention relates to a needle protection device that automatically recaps a used needle once it is withdrawn from the patient. The invention is comprised of a spiral type cut shield made of semi-rigid polymeric material that has an adhesive component on the face of the shield, which will come into contact with the patient's skin.

The shield is mounted onto a clear plastic base, which is located on a needle or syringe, and remains in a "relaxed" position until the device comes into contact with the patient's skin. When the needle is inserted into a patient, the shield attaches to the patient's skin through an adhesive component. As the needle is withdrawn, the adhesive component pulls the shield out of its "relaxed" position. The adhesive component holds the center portion of the shield to the patient's skin, placing the shield in tension as the needle is withdrawn from the patient. The tensile force created by the withdrawal of the needle is greater than the spring force effect of the shield, thereby forcing the spiral type cut shield to extend into a protective cone along the length of the needle. When the needle is fully withdrawn, the shield is a fully protective cone around the needle and needle tip. The adhesive component then releases from the patient's skin, retracting the center most portion of the shield to a cone-like shape around the needle. The needle tip prevents the shield from returning to its "relaxed" position by becoming fixed in the center most portion of the shield, thereby forcing the shield to remain as a protective cone along the entire length of the needle.

According a preferred embodiment, the shield is a round spiral type cut disk that is mounted onto the base of a needle.

According to another embodiment of the invention, the shield is mounted onto a cone that is then adhesively applied to the barrel of a syringe.

BRIEF DESCRIPTION OF THE DRAWINGS

The invention is described in greater detail in the following description of examples embodying the best mode of the invention, taken in conjunction with the drawing figures, in which:

FIG. 4 is a cut away side view of the needle protection device with a completely withdrawn right angle needle and the shield device has released from the patient's skin whereby the needle point has become fixed into the shield device;

FIG. 4A is a cut away side view of the needle protection device with a completely withdrawn straight needle and the shield device has released from the patient's skin whereby the needle point has become fixed into the shield device;

FIGS. 5 and 5A are top views of the spiral type cut shield according to the invention; and FIG. 6 is a cut away side view of the needle protection device mounted to a cone according to the invention.

DETAILED DESCRIPTION

Figure 1:
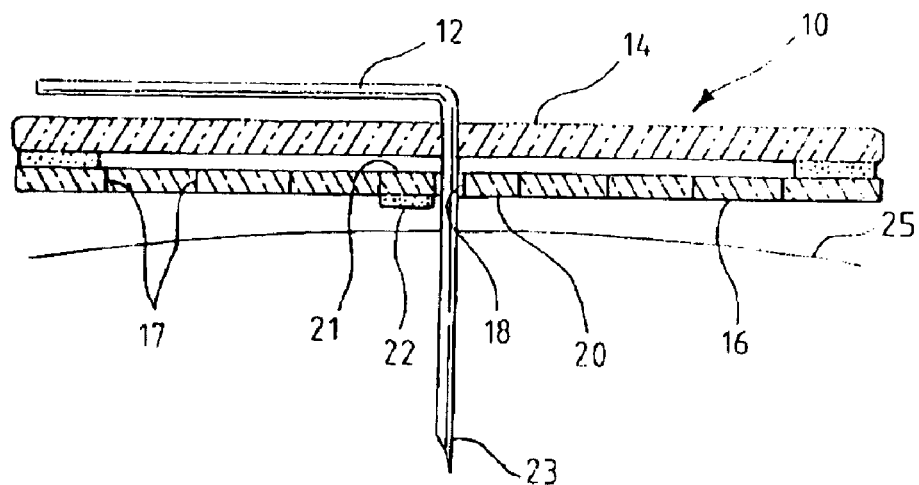
FIG. 1 is a cut away side view of the needle protection device with a right angle needle inserted in skin with the shield device in a "relaxed" position according to the invention.

For the purpose of promoting an understanding of the principles of the invention, reference will be made to the embodiments illustrated in the drawings. It will, nevertheless, be understood that no limitation of the scope of the invention is thereby intended, such alterations and further modifications in the illustrated device and such further applications of the principles of the invention illustrated herein being contemplated as would normally occur to one skilled in the art to which the invention relates.

Figure 1A:
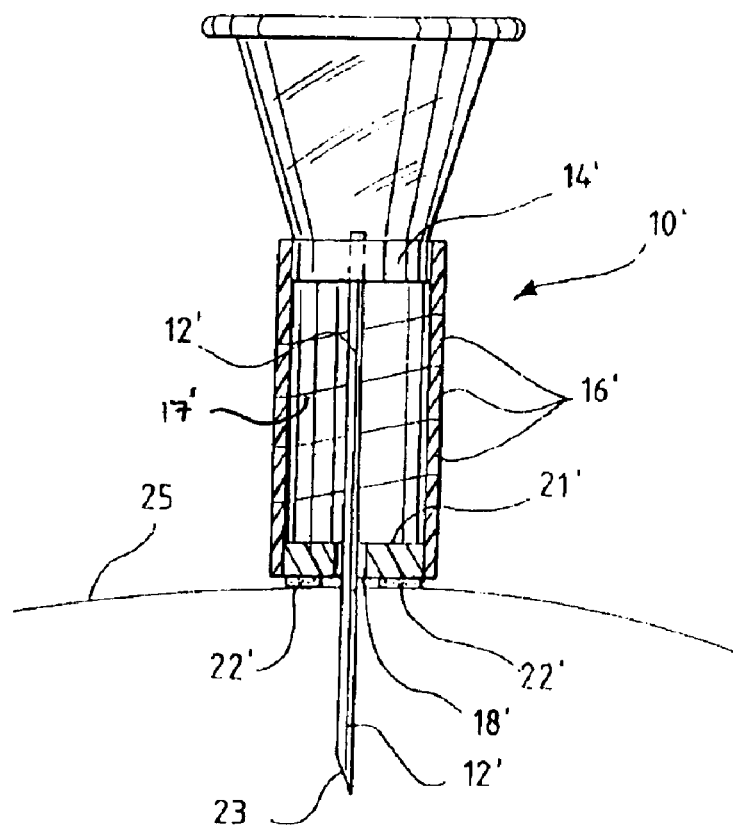
FIG. 1A is a cut away side view of the needle protection device with a straight needle inserted in skin with the shield device in a "relaxed" position according to the invention.

The needle safety and protection device 10 and 10' is attached to a conventional medical needle 12 and 12', and comprises a base 14 and 14', and a shield 16 and 16', as shown in FIGS. 1 and 1A. The base 14 and 14' is made of a semi-rigid polymeric material and is mounted on the needle 12 and 12' or on a support for the needle, at a distance sufficient to allow the needle 12 and 12' to enter human skin and perform its function appropriately.

Shield 16 and 16' is attached to the base 14 and 14' at the outer circumference of the base 14 and 14'. The shield 16 and 16' is attached to the base by way of adhesive, heat seal, or any suitable method, and is made of a semi-rigid polymeric material. The shield 16 and 16' has a spiral type cut 17 and 17', as shown in FIGS. 5 and 5A, to allow for extension of the shield 16 and 16' away from the base 14 and 14'. The shield 16 and 16' has an aperture 18 and 18' in its face 20 and 20'. The aperture 18 and 18' is slightly off-center on the face or surface 20 and 20' to prevent the tip 23 of the needle 12 and 12' from injuring the patient or a user, and the aperture 18 is large enough for the needle 12 and 12' to pass through. An adhesive 22 and 22' is attached loan outer portion of the face 20 and 20' of the shield 16 and 16' in a manner where it does not impede the movement of the needle 12 and 12' through the aperture 18 and 18' on the face 20 and 20' of the shield 16 and 16 As is shown in FIGS. 1 and 1A, when the needle 12 and 12' is inserted into a patient, through the skin 25 the shield 16 and 16' is in a "relaxed" or flat position wherein the adhesive 22 and 22' contacts the skin 25 of the patient. The adhesive 22 and 22' temporarily holds the face 20 and 20' of the shield 16 and 16' to the patient's skin.

Figure 2:
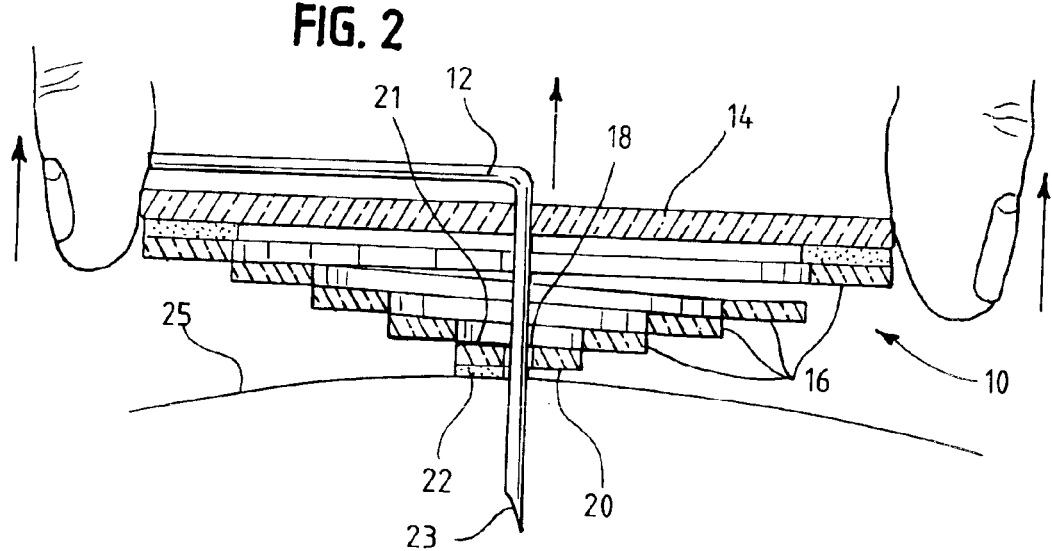
FIG. 2 is a cut away side view of the needle protection device as the right angle needle is being withdrawn from skin and an adhesive patch remains in contact with the skin whereby extending the shield according to the invention.
Figure 2A:
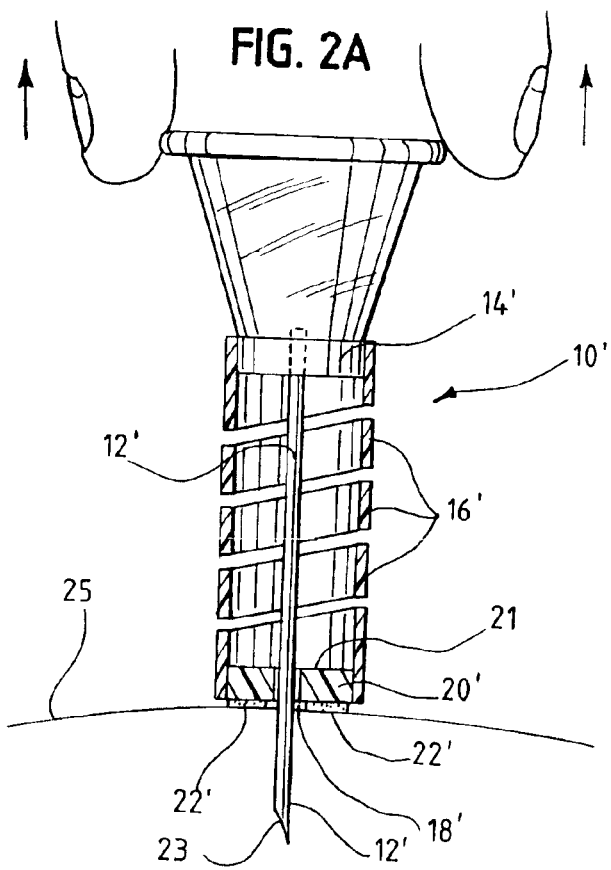
FIG. 2A is a cut away side view of the needle protection device as the straight needle is being withdrawn from skin and an adhesive patch remains in contact with the skin whereby extending the shield according to the invention.

As is shown in FIGS. 2 and 2A, as the needle 12 and 12' is withdrawn from the skin 25, the adhesive 22 and 22' remains in contact with the patient's skin and the tension force in shield 16 and 16' increases. The tensile force created by the withdrawal of the needle 12 and 12' is insufficient to break the force of the adhesive 22 and 22' holding shield 16 and 16' to the skin 25. This compels the spiral type cut shield 16 and 16' to extend into a protective cone shape along the length of the needle 12 and 12'. When the needle 12 and 12' is fully withdrawn from the patient, the needle 12 and 12' and needle tip are surrounded by and inside the fully extended protective shield 16 and 16'.

Figure 3:
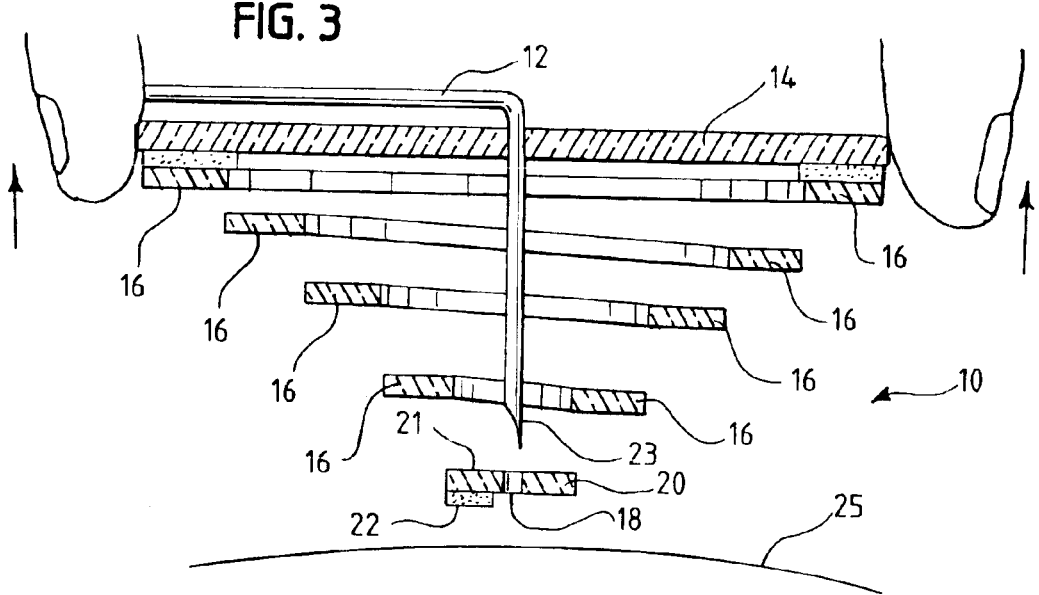
FIG. 3 is a cut away side view of the needle protection device with a right angle needle being withdrawn from the skin and the shield device is in an extended position according to the invention.
Figure 3A:
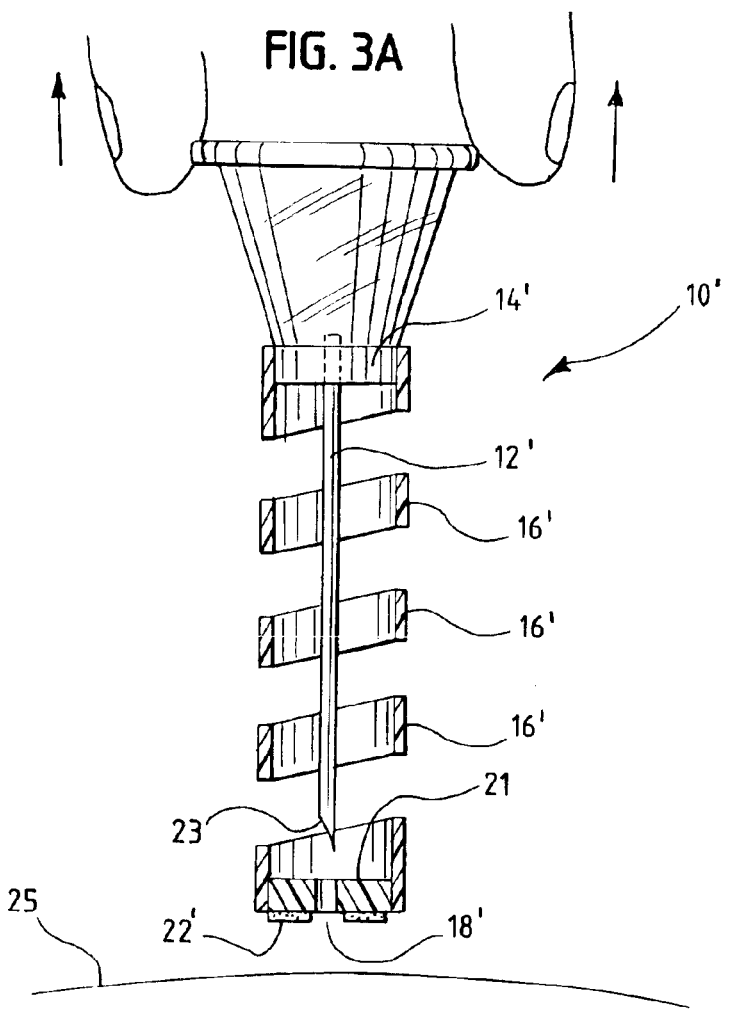
FIG. 3A is a cut away side view of the needle protection device with a straight angle needle being withdrawn from the skin and the shield device is in an extended position according to the invention.

As is shown in FIGS. 3 and 3A, when the needle 12 and 12' is completely withdrawn from the patient, the adhesive 22 and 22' releases from the patient's skin under the increase in tensile force created by the spiral cone formation of shield 16 and 16', and without affirmative action by a user. The shield 16 and 16' then begins to recoil back to the base 14 and 14'. However, as shown in FIGS. 4 and 4A, because the aperture 18 and 18' is slightly off center on the face 20 and 20' of the shield 16 and 16', the tip 23 of the needle 12 and 12' engages a portion of the inside face or surface 21 and 21' of the shield 16 and 16', and stops the shield 16 and 16' from recoiling into a fully relaxed position. Because the tip 23 of the needle 12 and 12' cannot again slide through the aperture 18 and 18', the face 20 and 20' of the shield 16 and 16' protects a user from being stuck by needle 12 and 12'.

In another embodiment of the invention, the shield 16 is attached to a cone 24, which is then fastened to a syringe 26, as shown in FIG. 6. The shield 16 operates the same way as described above whether it is attached to a needle 12 a needle housing or cone 24.

Various features of the invention have been particularly shown and described in connection with the illustrated embodiments of the invention. However, it must be understood that these particular products, and their method of manufacture, do not limit but merely illustrate, and that the invention is to be given its fullest interpretation within the terms of the appended claims.

I claim:

1. A self actuating needle safety device for use in medical procedures, comprising:
   a) a needle having at least one sharp tip;
   b) a base extending around the needle with the at least one sharp tip projecting outwardly from the base;
   c) a shield flexibly attached to an outer circumference of the base, the shield having a first and second surface and a spiral type cut to allow axial extension of said shield upon withdrawal of the needle;
   d) the shield also having an aperture through which the needle extends in an axial direction;
   e) an adhesive substance disposed on the first surface of the shield for temporary adhesion of the shield to a needle insertion area; and
   f) said shield flexibly extending from the base upon withdrawal of the needle from the needle insertion area, the at least one sharp tip of the needle being withdrawn from the aperture of the shield and engaging a portion of the second surface of the shield preventing said needle from re-entering the aperture.

2. A device according to claim 1, wherein the base is a clear plastic material.

3. A device according to claim 1, wherein the shield is a semi-rigid plastic material.

4. A device according to claim 1, wherein the needle is a right angle needle.

5. A needle safety device associated with a needle for use in medical procedures said needle having a tip for insertion into a needle insertion area, comprising:
   a shield adapted to be flexibly attached to the needle, said shield having a spiral type cut to allow said shield to extend in an axial direction upon withdrawal of said needle;
   an aperture extending through said shield, said aperture adapted to receive said needle;
   an adhesive disposed on an outwardly facing surface of said shield, said adhesive adapted to temporarily adhere said shield to said needle insertion area upon insertion of said needle into said needle insertion area;
   said adhesive adapted to releasably adhere said shield to said needle insertion area upon withdrawal of said needle from said needle insertion area, an inner surface of said shield adapted to receive the tip of said needle upon said withdrawal of said needle.

6. The needle safety device of claim 5, wherein said shield comprises a semi-rigid plastic material.

7. The needle safety device of claim 5, wherein said shield comprises a semi-rigid polymeric plastic material.

8. The needle safety device of claim 5, wherein the adhesive releases the shield from the needle insertion area upon withdrawal of the needle from the needle insertion area.

9. The needle safety device of claim 8, wherein the needle tip engages the inner surface of the shield upon release of said shield by said adhesive.

10. A needle safety device for use in medical procedures, comprising:
   a) a needle having at least one sharp tip;
   b) a base extending around the needle with the at least one sharp tip projecting from the base;
   c) a shield having a first and second surface; the second surface of the shield attached to the base; the shield having an aperture adapted to receive the needle and a spiral type cut to allow axial extension of said shield upon withdrawal of the needle;
   d) an adhesive disposed on the first surface of the shield said adhesive adapted to temporarily adhere the shield to a needle insertion area; and e) the shield flexibility extending from the base upon withdrawal of the needle from the needle insertion area, the at least one sharp tip of the needle passing through the aperture of the shield and engaging a portion of the second surface of the shield preventing the needle from re-entering the aperture.

11. A device according to claim 10, wherein the base is a clear plastic material.

12. A device according to claim 10, wherein the shield is a semi-rigid plastic material.

13. A device according to claim 12, wherein the shield is a polymeric plastic material.

14. A device according to claim 10, wherein the needle is a right angle needle.

* * * * *